(12) United States Patent
Isobe et al.

(10) Patent No.: US 10,172,694 B2
(45) Date of Patent: Jan. 8, 2019

(54) CROWN PROSTHESIS PREPARING SYSTEM, CROWN PROSTHESIS PREPARING METHOD, AND NON-TRANSITORY STORAGE MEDIUM STORING PROGRAM FOR PREPARING CROWN PROSTHESIS

(71) Applicant: Roland DG Corporation, Hamamatsu-shi, Shizuoka (JP)

(72) Inventors: Sachino Isobe, Hamamatsu (JP); Koji Saito, Hamamatsu (JP); Keiichi Niuishi, Hamamatsu (JP)

(73) Assignee: ROLAND DG CORPORATION, Shizuoka (JP)

( * ) Notice: Subject to any disclaimer, the term of this patent is extended or adjusted under 35 U.S.C. 154(b) by 0 days.

(21) Appl. No.: 15/704,127

(22) Filed: Sep. 14, 2017

(65) Prior Publication Data
US 2018/0078349 A1 Mar. 22, 2018

(30) Foreign Application Priority Data
Sep. 16, 2016 (JP) .................................. 2016-181689

(51) Int. Cl.
| | |
|---|---|
| *A61C 13/00* | (2006.01) |
| *A61C 13/08* | (2006.01) |
| *G06F 19/00* | (2018.01) |
| *A61C 5/77* | (2017.01) |
| *A61C 13/01* | (2006.01) |
| *A61C 13/09* | (2006.01) |

(52) U.S. Cl.
CPC ............ *A61C 13/0004* (2013.01); *A61C 5/77* (2017.02); *A61C 13/0006* (2013.01); *A61C 13/0022* (2013.01); *A61C 13/082* (2013.01); *G06F 19/00* (2013.01); *A61C 13/01* (2013.01); *A61C 13/09* (2013.01)

(58) Field of Classification Search
CPC .... A61C 13/0004; A61C 13/082; A61C 13/01
See application file for complete search history.

(56) References Cited

U.S. PATENT DOCUMENTS

| | | | | |
|---|---|---|---|---|
| 4,611,288 A | * | 9/1986 | Duret ................. | A61C 13/0004 700/163 |
| 5,343,391 A | * | 8/1994 | Mushabac .......... | A61C 13/0004 433/76 |
| 2004/0120781 A1 | * | 6/2004 | Luca .................. | A61C 13/0004 409/84 |

(Continued)

*Primary Examiner* — Ramesh B Patel
(74) *Attorney, Agent, or Firm* — Keating & Bennett, LLP

(57) ABSTRACT

A crown prosthesis preparing system includes a data generator and a cutting device including a retainer, a cutting mechanism, and a controller. The cutting mechanism includes a first processing tool that cuts a workpiece to form a processed workpiece, a second processing tool that polishes the processed workpiece, a driver detachably holding at least one of the first processing tool and the second processing tool and controlling its position. The controller includes a first control section causing the first processing tool to cut the workpiece retained by the retainer based on three-dimensional data, to form the processed workpiece, and a second control section causing the second processing tool to polish a surface of the processed workpiece retained by the retainer based on the three-dimensional data.

9 Claims, 10 Drawing Sheets

(56) References Cited

U.S. PATENT DOCUMENTS

| | | | |
|---|---|---|---|
| 2005/0142517 A1* | 6/2005 | Frysh | A61C 9/0053 433/173 |
| 2005/0186540 A1* | 8/2005 | Taub | A61C 13/0004 433/223 |
| 2006/0093985 A1* | 5/2006 | Matsuda | A61C 13/0004 433/50 |
| 2008/0090207 A1* | 4/2008 | Rubbert | A61C 5/007 433/171 |
| 2008/0228303 A1* | 9/2008 | Schmitt | A61C 13/0004 700/98 |
| 2009/0042167 A1* | 2/2009 | Van Der Zel | A61C 1/084 433/215 |
| 2009/0275000 A1* | 11/2009 | Jung | A61C 13/0004 433/223 |

\* cited by examiner

CROWN PROSTHESIS PREPARING SYSTEM, CROWN PROSTHESIS PREPARING METHOD, AND NON-TRANSITORY STORAGE MEDIUM STORING PROGRAM FOR PREPARING CROWN PROSTHESIS

CROSS REFERENCE TO RELATED APPLICATIONS

This application claims the benefit of priority to Japanese Patent Application No. 2016-181689 filed on Sep. 16, 2016. The entire contents of this application are hereby incorporated herein by reference.

BACKGROUND OF THE INVENTION

1. Field of the Invention

The present invention relates to a crown prosthesis preparing system and a crown prosthesis preparing method for preparing a crown prosthesis, as well as a non-transitory storage medium storing a program for preparing a crown prosthesis.

2. Description of the Related Art

Crown prostheses (also referred to as artificial teeth and artificial dental crowns, for example) have been prepared by cutting a workpiece, such as one made of a ceramic material or a resin material, into a desired shape. The cutting of a crown prosthesis was carried out manually in the past, but with the introduction of computer-aided design (CAD) and computer-aided manufacturing (CAM) technology in recent years, it has become commonplace to carry out the cutting using a cutting device based on data generated by a computer.

Generally, in this CAD/CAM technology, an abutment tooth model that imitates the shape of a patient's tooth is scanned to obtain three-dimensional data. Subsequently, based on the three-dimensional data, the shape of a desired crown prosthesis is designed by CAD to create STL data. Then, based on such design, cutting process data that are readable by a cutting device are produced with CAM software. The cutting process data include, for example, the type of the cutting tool to be used that cuts, and the information concerning tool path, such as the way of moving the cutting tool (position, angle, trail, and moving speed). Then, based on the cutting process data, the cutting device cuts a workpiece material for crown prosthesis.

An example of the workpiece material that has been used in recent years is a zirconia-based material, which has high biocompatibility and yields high strength by sintering. This has enabled preparation of crown prostheses by what is called a full-contour technique, in which a workpiece material is cut to the final contour by a cutting device. However, zirconia does not provide sufficient translucency for crown prostheses for anterior teeth, which require high esthetics. For this reason, only the frame portion (also referred to as "coping") that serves as the foundation of dental crown is made of a zirconia-based material, and a porcelain material with an appropriate color tone or texture suitable for each patient is layered (hand-layered) on the frame portion by a dental technician, to complete the crown prosthesis.

In addition, in the cutting process of crown prostheses by the CAD/CAM technology, a corresponding cutting tool is brought into contact with a workpiece material based on the information contained in the cutting process data with predetermined conditions such as angles and trails, to cut the workpiece material to prepare a crown prosthesis with a target three-dimensional shape. Consequently, it is inevitable that the surface of the crown prosthesis after the cutting unavoidably has cutting streaks (cutting marks), which are streaky surface irregularities that originate from the trails or the like of the cutting tool. Such surface irregularities aesthetically spoil the appearance of the crown prosthesis. Moreover, they are feared to cause disorders in the senses of taste and touch of tongue, and cause the accumulation of dental plaque, which stimulates the gum, resulting in periodontitis. For this reason, the crown prosthesis prepared by the CAD/CAM technology inevitably requires the work of polishing the surface thereof by a dental technician before or after sintering the crown prosthesis to remove the surface irregularities. Under such circumstances, zirconia-based workpiece materials that achieve high strength and high translucency after sintering have been developed recently.

SUMMARY OF THE INVENTION

In view of the foregoing and other problems, preferred embodiments of the present invention provide crown prosthesis preparing systems and a crown prosthesis preparing methods that reduce the amount of time and effort required for workers to prepare a crown prosthesis.

A crown prosthesis preparing system according to a preferred embodiment of the present invention includes: a data generator producing three-dimensional data representative of a crown prosthesis; and a cutting device including a retainer retaining a workpiece, a cutting mechanism cutting the workpiece, and a controller controlling the retainer and the cutting mechanism. The cutting mechanism includes a first processing tool that cuts the workpiece to form a processed workpiece, a second processing tool that polishes the processed workpiece having been formed, and a driver detachably holding at least one of the first processing tool and the second processing tool and controlling a position of the at least one of the first processing tool and the second processing tool relative to the workpiece. The controller is configured or programmed to include a first control section controlling the retainer and the cutting mechanism based on the three-dimensional data to cause the first processing tool to cut the workpiece retained by the retainer, so as to form the processed workpiece; and a second control section controlling the retainer and the cutting mechanism based on the three-dimensional data to cause the second processing tool to polish a surface of the processed workpiece retained by the retainer.

A crown prosthesis preparing system according to a preferred embodiment of the present invention is provided with the first processing tool that cuts and the second processing tool that polishes. The first processing tool cuts a crown prosthesis in a target shape out of a workpiece, which is a material used to provide the crown prosthesis, based on three-dimensional data. Thereafter, the crown prosthesis that has been cut out is successively polished. This makes it possible to prepare a crown prosthesis having a shape corresponding to the final contour, for example, without surface irregularities that are caused by the cutting. Because the cutting and the polishing mentioned above are carried out based on the three-dimensional data, it is possible to easily and accurately prepare a crown prosthesis that achieves pre-designed occlusion. This saves the amount of time and effort of the operator in preparing the crown prosthesis.

Preferred embodiments of the present invention provide crown prosthesis preparing systems that reduce the amount of time and effort required for the operator to prepare a crown prosthesis. Preferred embodiments of the present invention also provide crown prosthesis preparing methods that use the crown prosthesis preparing systems, and non-transitory storage media storing programs used to prepare a crown prosthesis.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
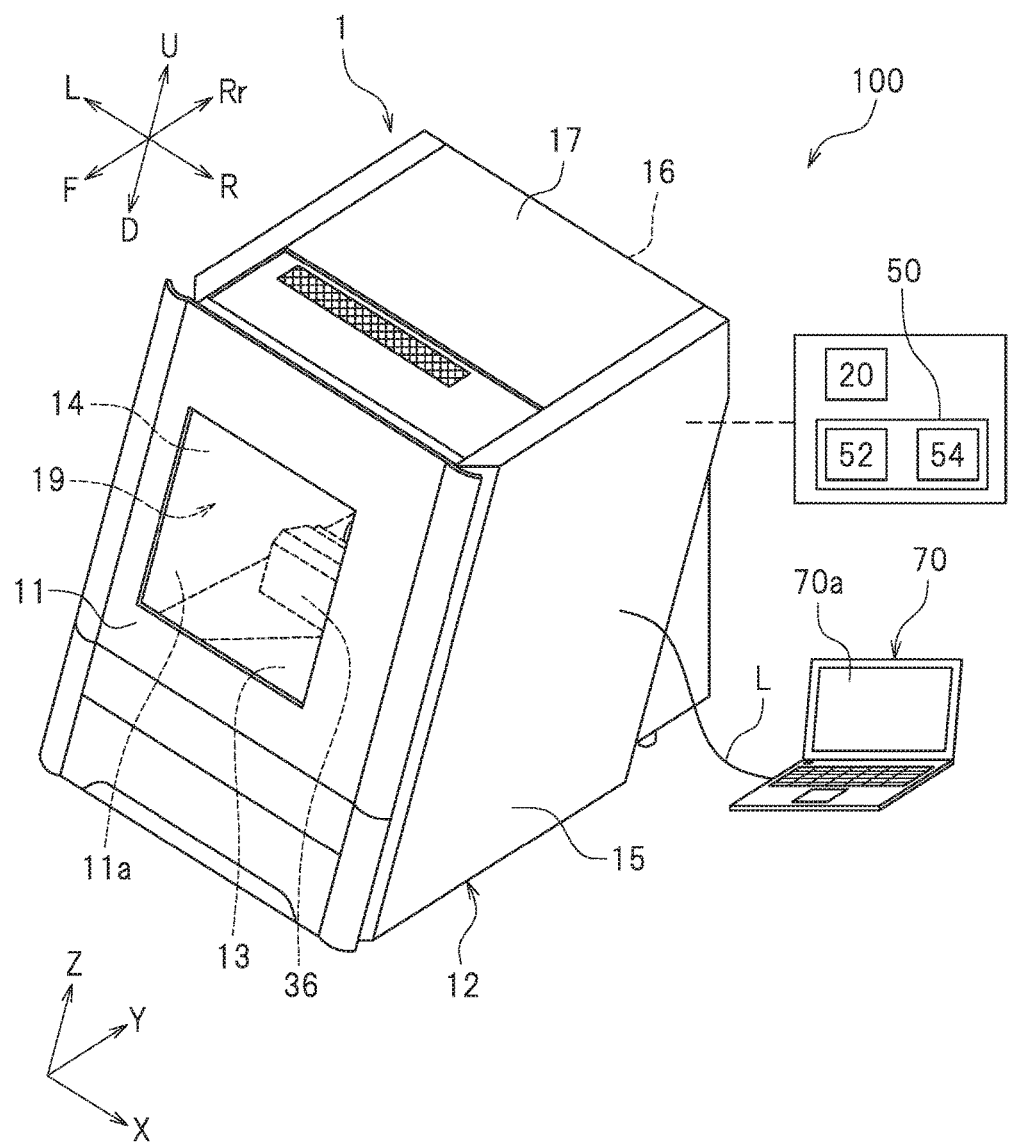
FIG. 1 is a perspective view illustrating the structure of a crown prosthesis preparing system according to a preferred embodiment of the present invention.

A crown prosthesis preparing system 100 and a crown prosthesis preparing method, according to a preferred embodiment of the present invention, will be described below. As illustrated in FIG. 1, a crown prosthesis preparing system 100 includes a cutting device 1 and a data generator 70. This crown prosthesis preparing system 100 prepares a crown prosthesis to restore a defect portion that has occurred in a portion or the whole of a patient's natural tooth by covering at least a portion or the whole of an abutment tooth provided in the patient's oral cavity, such that the crown prosthesis has properties and appearance similar to the natural tooth. In particular, the crown prosthesis preparing system 100 disclosed herein suitably prepares a crown prosthesis for an anterior tooth, which requires high esthetics.

FIG. 1 shows an example in which the crown prosthesis preparing system 100 has only one cutting device 1, for example. However, it is also possible that the crown prosthesis preparing system 100 may include a plurality of cutting devices 1. When the crown prosthesis preparing system 100 includes a plurality of cutting devices 1, the plurality of cutting devices 1 may have the same structure. The cutting device 1 and the data generator 70 are connected by a line L so that they can be in wired communication with each other. The cutting device 1 and the data generator 70 may also communicate wirelessly with each other. As the data generator 70, it is possible to adopt a CAD/CAM device in which a CAD function and a CAM function are combined. The CAD/CAM device in the present example is constructed by introducing a program that implements the CAD function and the CAM function into a personal computer. This personal computer is furnished with a display device, such as a display 70a, and an input device, such as a keyboard, a touch screen, or a mouse. However, the data generator 70 is not limited to the CAD/CAM device.

Figure 2A:
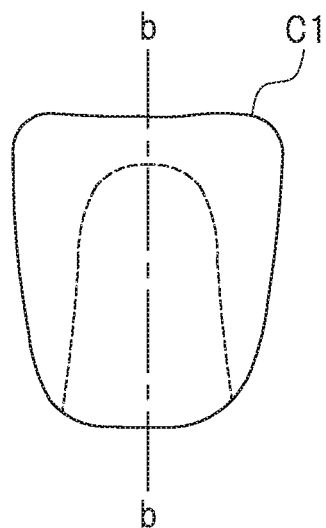
FIG. 2A is a front view schematically illustrating a crown prosthesis.
Figure 2B:
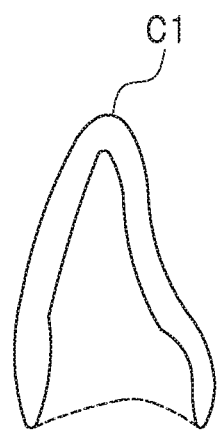
FIG. 2B is a cross-sectional view taken along line b-b in FIG. 2A.
Figure 2C:
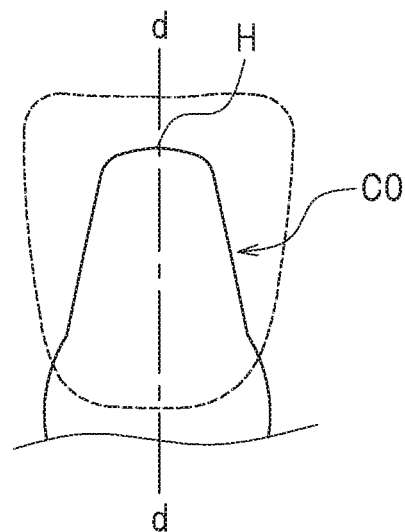
FIG. 2C is a front view schematically illustrating an abutment tooth.
Figure 2D:
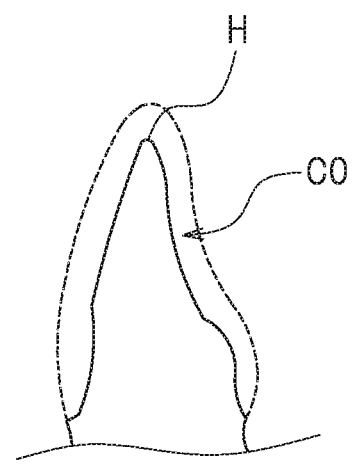
FIG. 2D is a cross-sectional view taken along line d-d in FIG. 2C.

FIG. 2A is a front view of a crown prosthesis C1 to be prepared by the crown prosthesis preparing system 100, and FIG. 2B is a cross-sectional view taken along line b-b in FIG. 2A. FIG. 2C is a front view of an abutment tooth C0, to which the crown prosthesis C1 is to be fitted, and FIG. 2D is a cross-sectional view taken along line d-d in FIG. 2C. As illustrated in FIG. 2A, the crown prosthesis C1 has a shape that imitates a crown portion of a natural tooth, which is exposed from the gum. The abutment tooth C0 is buried in the patient's gum, and defines and functions as a dental root to support the crown prosthesis C1. The crown prosthesis C1 is fitted and fixed onto a head portion H of the abutment tooth C0, whereby an artificial tooth is completed.

The crown prosthesis C1 of the present example may be composed of, for example, a zirconia-based ceramic material. In the preparation of the crown prosthesis C1 utilizing the CAD/CAM technology, the crown prosthesis C1 as shown in FIGS. 2A and 2B, for example, is shaped by cutting a disk-shaped workpiece made of a zirconia-based ceramic material with the use of the cutting device 1. Conventionally, for the crown prostheses for anterior teeth, which require high esthetics, additional facing (hand-layering) using a translucent porcelain material has been essential, and such a porcelain material has formed the final contour of the crown prosthesis. However, workpieces made of a zirconia-based ceramic with improved color tone and translucency have become available recently. The present inventors have investigated a way of shaping a crown prosthesis C1 without necessitating the facing of a porcelain material. In the technology disclosed herein, after cutting of the crown prosthesis C1, the crown prosthesis C1 that has been cut is polished using the cutting device 1, and adjustment of the final contour of the crown prosthesis C1 is also carried out using the cutting device 1. In other words, the final contour of the crown prosthesis C1 is shaped by cutting.

Figure 3:
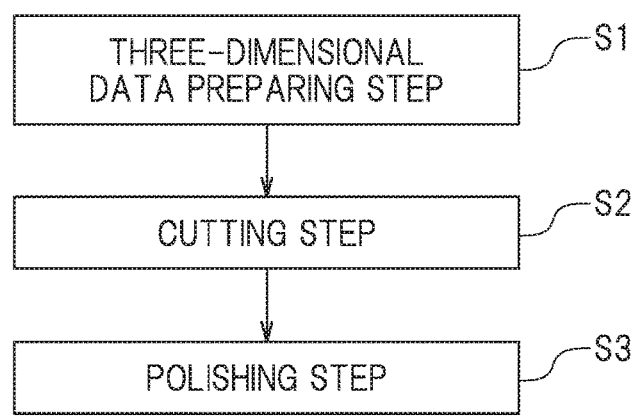
FIG. 3 is a flow-chart illustrating a crown prosthesis preparing method according to a preferred embodiment of the present invention.
Figure 4A:
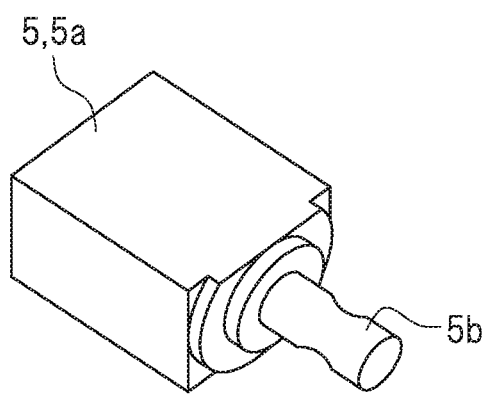
FIG. 4A is a perspective view illustrating an example of a workpiece.
Figure 4B:
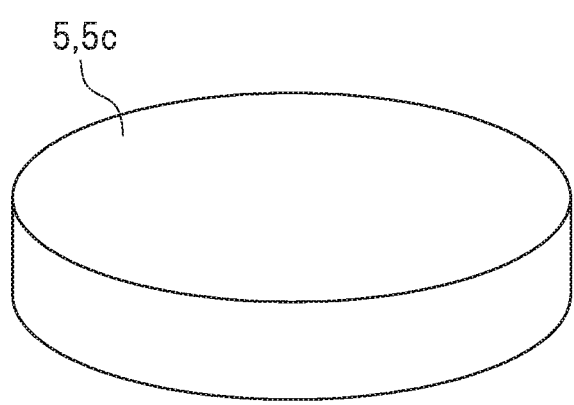
FIG. 4B is a perspective view illustrating another example of a workpiece.

Specifically, the crown prosthesis preparing method disclosed herein substantially includes, as shown in FIG. 3, the following steps S1 to S3.
- (S1) Three-dimensional data preparing step
- (S2) Cutting step
- (S3) Polishing step S1. Three-Dimensional Data Preparing Step The data generator 70 produces three-dimensional data that are readable by the cutting device 1, to prepare the crown prosthesis C1. The three-dimensional data may be, for example, in STL (Standard Triangulated Language) format. The data generator 70 forms appropriate three-dimensional data according to the form of workpiece to be processed. For example, a workpiece 5 may be a pin block material 5a as illustrated in FIG. 4A, from which one or a plurality of crown prostheses C1 can be prepared and which is provided with a connection pin 5b that is connectable to the cutting device 1, and a large-sized block material 5c as illustrated in FIG. 4B, from which a plurality of crown prostheses C1 can be prepared, both of which are available on the market. When the pin block material 5a is used, for example, the data generator 70 may produce three-dimensional data representative of the crown prosthesis C1 only. When the large-sized block material 5c is used, for example, the data generator 70 may produce first data, which are three-dimensional data representative of a first member C3 (see FIG. 5A), in which a support portion S is connected to the crown prosthesis C1. The following describes an example in which the crown prosthesis C1 is prepared using the first data.

Figure 5A:
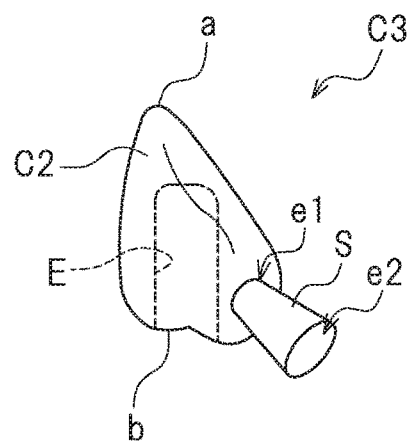
FIG. 5A is a view illustrating an image of first data according to a preferred embodiment of the present invention.
Figure 5B:
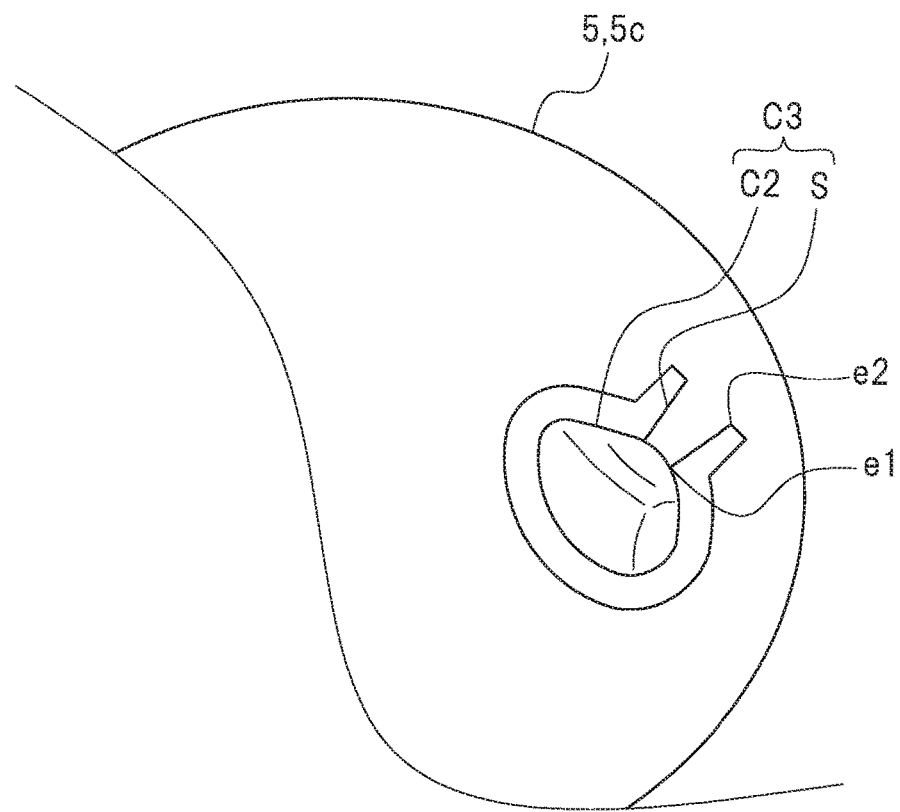
FIG. 5B is a view for illustrating the arrangement of the first data in a workpiece.

FIG. 5A illustrates an image of the first member C3 represented by the first data. The first data are three-dimensional data representative of the crown portion C2, which corresponds to the target crown prosthesis C1, and the first member C3, which as the support portion S for supporting the crown portion C2. As illustrated in FIG. 5B, the support portion S is a rod-shaped member that secures a crown portion C2 to the block material 5c. In cutting out the crown portion C2 from the block material 5c, the support portion S to prevents the crown portion C2 that has been cut out from dropping off. Moreover, in the technology disclosed herein, the support portion S prevents the crown portion C2 from dropping in the later-described cutting step, and additionally defines and functions as a support member to support the crown portion C2 in the polishing step.

The first data may be prepared, for example, by the operator in such a manner that the three-dimensional shape of the first member C3 is designed by CAD of the data generator 70 to form STL data, and the cutting process data are produced from such a design with CAM. In designing the first member C3, based on the three-dimensional data of the abutment tooth C0 and the dental arch in the patient's oral cavity, the three-dimensional shapes of the crown portion C2 and the support portion S are designed so that a desired crown prosthesis C1 can be obtained. The three-dimensional data of the abutment tooth C0 can be obtained by directly non-contact scanning the dental arch contours in the patient's intraoral cavity (laser scanning or scanning with a CCD sensor) or by scanning a model of the dental arch and the abutment tooth. The data generator 70 may receive the three-dimensional data of the dental arch and the abutment tooth C0, for example, through the Internet. The images represented by the three-dimensional data received by the data generator 70 can be observed on the display 70a (see FIG. 1) of the data generator 70.

The crown portion C2 is formed in a crown shape such as to cover the abutment tooth C0. The crown portion C2 has a recessed portion E in the dental root side b of the crown portion C2, corresponding to the shape of the abutment tooth C0 so that it can fit with the abutment tooth C0. The contour of the crown portion C2 may be designed taking into consideration such things as matching with surrounding teeth, occlusion, and preferences of the patient or the operator.

The support portion S is preferably rod shaped and protrudes from the outer surface of the crown portion C2. Conventionally, a plurality of support portions, typically two or three support portions, are provided for one crown portion C2 and arranged evenly at the peripheral edge of the crown portion C2 so that, during cutting, the crown portion C2 is able to be supported evenly, stably, and with a smaller connection area. However, in the technology disclosed herein, it is preferable, but not required, that only one support portion S be provided for one crown portion C2. In this case, in order to ensure sufficient support strength, the support portion S may have a larger cross-sectional area than the conventional support portions connected to the crown portion C2. In addition, the support portion S is provided elevatingly on the tongue side surface, not on the lip side surface, of the crown portion C2. This prevents poor esthetics associated with the later removal of the support portion S. It should be noted that in the present description, the term "tongue side" merely means the inner side of a dental arch, the side that faces the tongue, or the side that faces the lips. Accordingly, the term "tongue side" herein is not limited to the tongue side in the lower jaw but is meant to include the tongue side in the upper jaw as well.

The shape of the support portion S is not limited to a particular shape, and may be substantially a cylindrical shape, for example. It should be noted that the conventional support portion has a generally uniform width (for example, start point diameter: about 2.5 mm, end point diameter: about 3 mm) along its length. In contrast, in the technology disclosed herein, the support portion S may have a uniform width (size) or different widths (sizes) along its length. For example, the support portion S may be designed so that the cross-sectional area of a first end portion e1 of the support portion S, which is an end portion thereof connected to the crown portion C2, is smaller than the cross-sectional area of a second end portion e2 of the support portion S, which is an end portion thereof opposite to the first end portion e1. As illustrated in FIG. 5B, the second end portion e2 is connected to the workpiece 5. For example, when the support portion S is in a cylindrical shape, the cross-sectional diameter of the first end portion e1 may be smaller than the cross-sectional diameter of the second end portion e2. As an example, when the cross-sectional diameter of the first end portion e1 is from about 2 mm to about 3 mm (typically about 2.5 mm), it is preferable that the cross-sectional diameter of the second end portion e2 be set in a range of greater than about 3 mm to about 5 mm, for example, from about 4 mm to about 5 mm (typically about 4.5 mm). When this is the case, the proportion of the cross-sectional diameter of the second end portion e2 to the cross-sectional diameter of the first end portion e1 may be from about 1.3 times to about 2 times, for example, as a guideline. In the present preferred embodiment, the support portion S preferably is designed to be in a cylindrical shape such that the cross-sectional diameter of the first end portion e1 is about 2.5 mm and the cross-sectional diameter of the second end portion e2 is about 4.5 mm, for example. This enables the crown portion C2 to be supported firmly during later-described cutting step and polishing step, and also makes it possible to reduce the area of the removal marks that are left on the crown portion C2 when the support portion S is removed after the polishing step.

In addition, when a completely sintered zirconia-based ceramic material is used as the workpiece 5 for forming the crown portion C2, the efficiency of the cutting process becomes considerably low. Thus, a semi-sintered zirconia-based ceramic material, with which sintering can progress by firing, may be preferably used as the workpiece 5. Here, the semi-sintered zirconia-based ceramic material means a material obtained by pre-sintering a ceramic green compact (unsintered compact) at a temperature lower than the final sintering temperature. The semi-sintered ceramic material undergoes densification by firing, resulting in volumetric contraction, when it is completely sintered. Accordingly, in producing the first data, densification by the complete sintering is taken into consideration, and the first data are produced in a larger size such that the sintering contraction is able to be compensated. The volumetric contraction in complete sintering may be considered to be about 17% to about 22% (typically about 20%), although it may vary because it depends on the composition, the material particle size, the compressive strength, the degree of pre-sintering, etc. of the workpiece 5. The information concerning the size and contraction rate of the workpiece 5 can be provided to the data generator 70 from, for example, a flash memory, a memory chip, or the like that is attached to the workpiece 5. For example, when a disk-shaped block material 5c as illustrated in FIG. 5B is used as the workpiece 5, the first data may contain position information indicating from what position of the disk-shaped block material 5c and in what posture the first member C3 should be cut out. The first data produced in this way are then sent to a later-described storage or memory 20 (see FIG. 1) of the cutting device 1.

It is possible to use as the block material 5c, for example, a semi-sintered zirconia compact that is homogeneous over the entire compact and is white and monochromatic, or a semi-sintered zirconia compact with improved design. The semi-sintered zirconia compact with improved design may be a semi-sintered zirconia compact that is uniformly colored over the entire compact. Alternatively, the block material 5c may be an optically-gradational block (for example, optically-gradational disk) in which at least one of brightness and hue successively changes along one axis of the sintered compact after complete sintering. This optically-gradational block may have, for example, a layered structure in which a plurality of layers each designed to have slightly different brightness and/or hue after sintering are stacked in a thickness direction. The present preferred embodiment uses an optically-gradational disk that is in a circular disk shape and has a four-layer structure in which the brightness and hue gradually change along its thickness direction. As for the posture in which the first member C3 is cut out of such an optically-gradational disk, the first data are produced so that the tip end side a of the crown portion C2 is disposed in a layer with a higher brightness and the dental root side b thereof is disposed in a layer with a lower brightness. This makes it possible to form a crown portion C2 with its appearance similar to a natural tooth.

S2. Cutting Step

In the cutting step, a workpiece is cut by the cutting device 1 based on the first data (three-dimensional data) to form the first member C3 as a processed workpiece.

Figure 6:
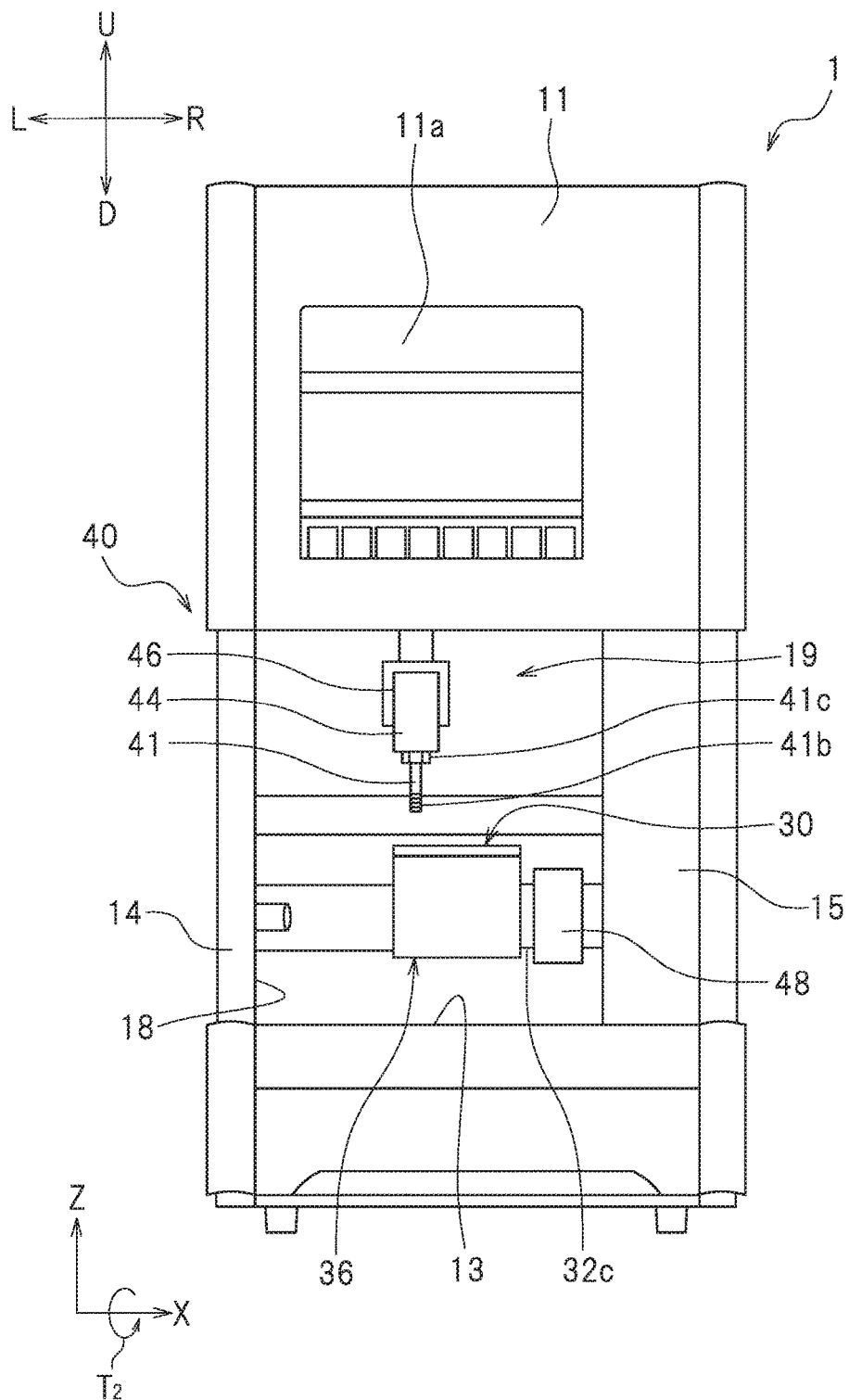
FIG. 6 is a front view illustrating a cutting device according to a preferred embodiment of the present invention with its front cover being opened.

First, the structure of the cutting device 1 according to a preferred embodiment of the present invention will be described with reference to the drawings as appropriate. FIG. 6 is a front view illustrating the cutting device 1 shown in FIG. 1 in a state in which a front cover 11 is open. In the following description, the terms "left" and "right" respectively mean left and right as defined based on the perspective of the operator facing the front of the cutting device 1. A bottom wall 13 of the cutting device 1, which will be described later, is inclined downward from the front toward the back as viewed from the perspective of the operator. Accordingly, a direction approaching toward the operator along the bottom wall 13 is defined as "frontward," and a direction away from the operator along the bottom wall 13 is defined as "rearward." In addition, an ascending direction orthogonal to the bottom wall 13 is defined as "upward", and a descending direction orthogonal thereto is defined as "downward". Reference characters F, Rr, L, R, U, and D in the drawings represent front, rear, left, right, up, and down, respectively. The X axis extends along a left-right direction. The Y axis extends along a front-rear direction. The Z axis extends along an up-down direction. These directional terms are, however, merely provided for purposes in illustration and are not intended to limit the preferred embodiments of the cutting device 1 in any way.

As illustrated in FIG. 1, the cutting device 1 is formed in a box shape. The cutting device 1 includes a case main body 12 and a front cover 11. The case main body 12 includes a bottom wall 13, a left wall 14 extending upward from the leftmost end of the bottom wall 13, a right wall 15 extending upward from the rightmost end the bottom wall 13, a rear wall extending upward from the rearmost end of the bottom wall 13, and a top wall 17 connecting the uppermost ends of the left wall 14, the right wall 15, and the rear wall 16. As illustrated in FIG. 6, the front portion of the case main body 12 includes an opening. An opening is surrounded by the bottom wall 13, the left wall 14, the right wall 15, and the top wall 17. The front cover 11 is able to move upward and downward along the front end of the left wall 14 and the front end of the right wall 15 so as to be openable/closable. When the front cover 11 moves upward, the inside and outside of the case main body 12 are allowed to be in communication with each other. The front cover 11 is provided with a window portion 11a. The operator can visually observe the internal space through the window portion 11a.

A processing area 19 of the internal space is surrounded by the bottom wall 13, the left wall 14, the right wall 15, the rear wall 16, and the top wall 17. In the processing area 19, a cutting process for a disk-shaped workpiece 5, for example, is carried out. By cutting the workpiece 5, one crown prosthesis C1 or two or more crown prostheses C1 is/are milled out of the workpiece 5. In addition, a control area, not shown, is provided inside the right wall 15 of the cutting device 1. The processing area 19 is a space wider than the control area. The control area accommodates, for example, a driver (not shown) that controls rotation and movement of a retainer 30 and a magazine 48, which will be described later. The right wall 15 has a box shape with a detachable cover so that the control area therein is provided in a closed region.

A rear inner wall (not shown) disposed vertically is provided at the rear end of the bottom wall 13. The top end of the rear inner wall is connected to the top wall 17. The rear area between the rear wall 16 and the rear inner wall accommodates a controller 50 and a storage or memory 20 (see FIG. 1), which will be described later. As illustrated in FIG. 6, the retainer 30 that retains the workpiece 5 and a cutting mechanism 40 that cuts the workpiece 5 are provided in the processing area 19.

Figure 7:
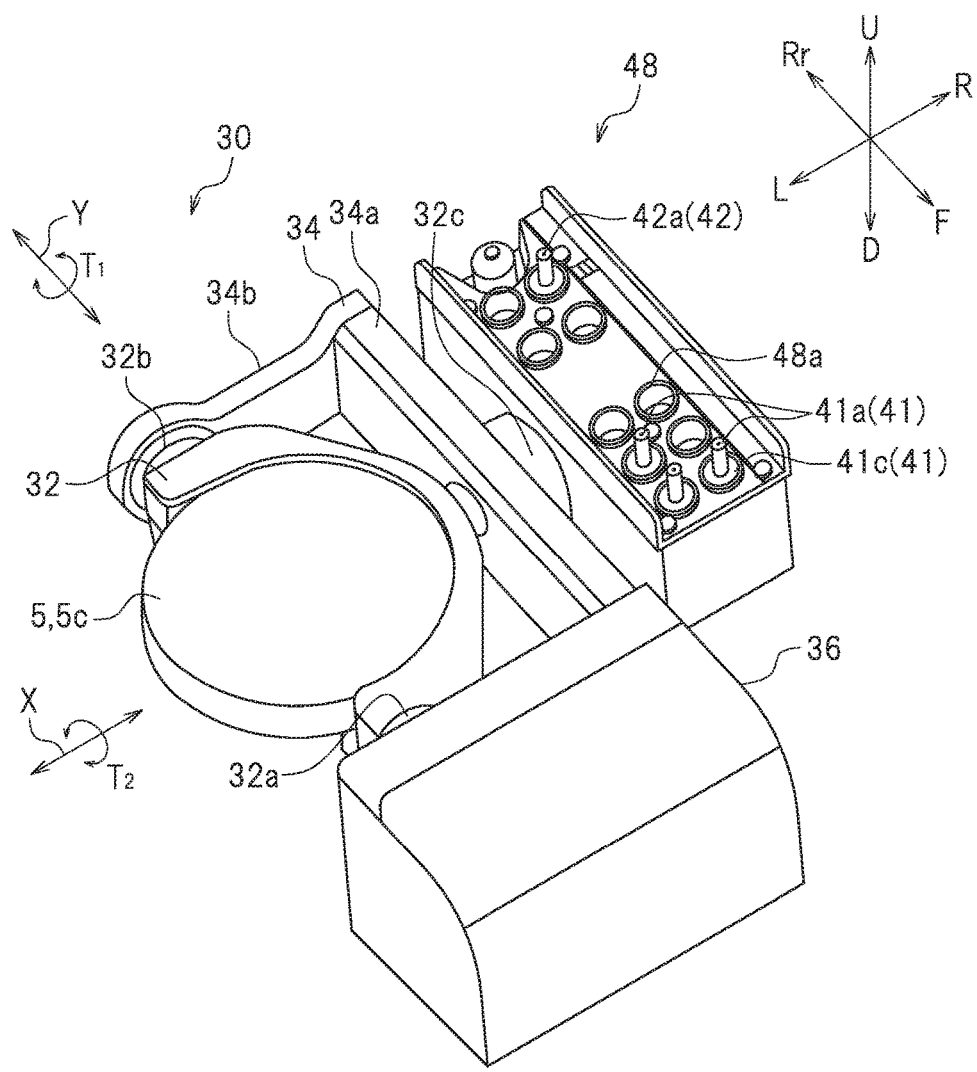
FIG. 7 is a perspective view illustrating a disk-shaped workpiece held by a retaining portion according to a preferred embodiment of the present invention.

In the example shown in FIG. 7, the workpiece 5 is a large-sized disk-shaped block material 5c. The block material 5c is securely retained by the retainer 30. The retainer 30 includes a first retaining portion 32 with a semi-circular arc shape. A first rotary shaft 32a is connected to a front portion of the first retaining portion 32, and a second rotary shaft 32b is connected to a rear portion of the first retaining portion 32. The first rotary shaft 32a and the second rotary shaft 32b have a common rotational axis, which extends along the Y axis. The first rotary shaft 32a is connected to a driver 36, which is provided in front of the first retaining portion 32. The driver 36 may be a motor, for example. The driver 36 can rotate the first rotary shaft 32a in directions T1 about the Y axis. This enables the workpiece 5 (i.e., the block material 5c) to rotate in the directions T2 via the first retaining portion 32.

An L-shaped second retaining portion 34 is coupled to a rear end portion of the driver 36. The rear edge portion of the driver 36 and the L-shaped second retaining portion 34 together define an angular C-shaped structure. The first retaining portion 32 is coupled to and supported by the driver 36 and the L-shaped second retaining portion 34, which define the angular C-shaped structure. The semi-circular arc-shaped first retaining portion 32 is supported by the angular C-shaped structure defined by the driver 36 and the second retaining portion 34 so as to be surrounded by the angular C-shaped structure. The second retaining portion 34 includes a first member 34a extending along the Y axis and a second member 34b extending along the X axis. The second rotary shaft 32b is supported at an end of the second member 34b of the second retaining portion 34, and the driver 36 is supported at an end of the first member 34a. In addition, a third rotary shaft 32c is connected to the first member 34a of the second retaining portion 34 at a position corresponding to the center along the Y axis of the semi-circular arc-shaped first retaining portion 32. The third rotary shaft 32c is connected to a driver, which is not shown in the drawings, so as to rotate the second retaining portion 34 in directions T2 about the X axis. This enables the workpiece 5 to rotate in the directions T2 via the first retaining portion 32 and the second retaining portion 34. Thus, the retainer 30 retains the workpiece 5 so as to be rotatable in the directions T1 and the directions T2. Moreover, the second retaining portion 34 is movable along the X axis via another driver, which is not shown in the drawings. This enables the workpiece 5 to move along the X axis via the first retaining portion 32 and the second retaining portion 34.

Next, the cutting mechanism 40 will be described. As illustrated in FIGS. 6 to 8, the cutting mechanism 40 includes a first processing tool 41 and a second processing tool 42. The rod-shaped first processing tool 41 is used that cuts the workpiece 5. The rod-shaped second processing tool 42 is used that polishes the processed workpiece that has been formed by the cutting process. As illustrated in FIG. 7, the cutting mechanism 40 includes a magazine 48 that accommodates the first processing tool 41 and the second processing tool 42. In order to accommodate and store the first processing tool 41 and the second processing tool 42 in predetermined positions, the magazine 48 is provided with a plurality of hole-shaped stockers 48a at the predetermined positions.

Figure 8A:
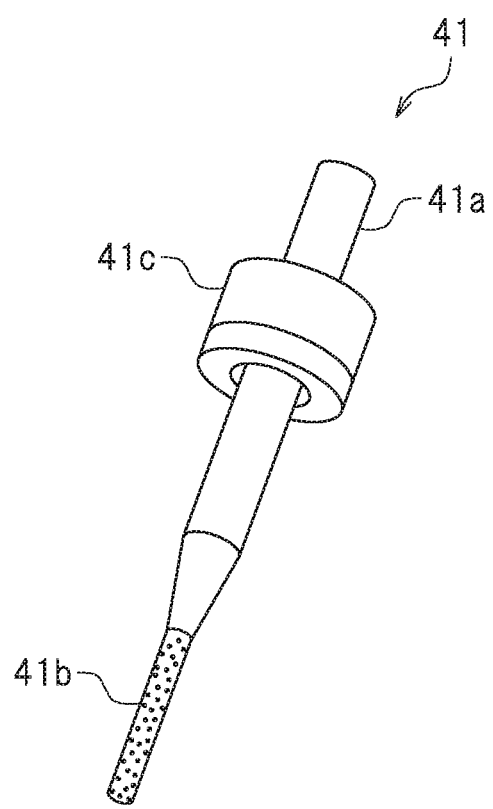
FIG. 8A is a perspective view illustrating a first processing tool according to a preferred embodiment of the present invention.
Figure 8B:
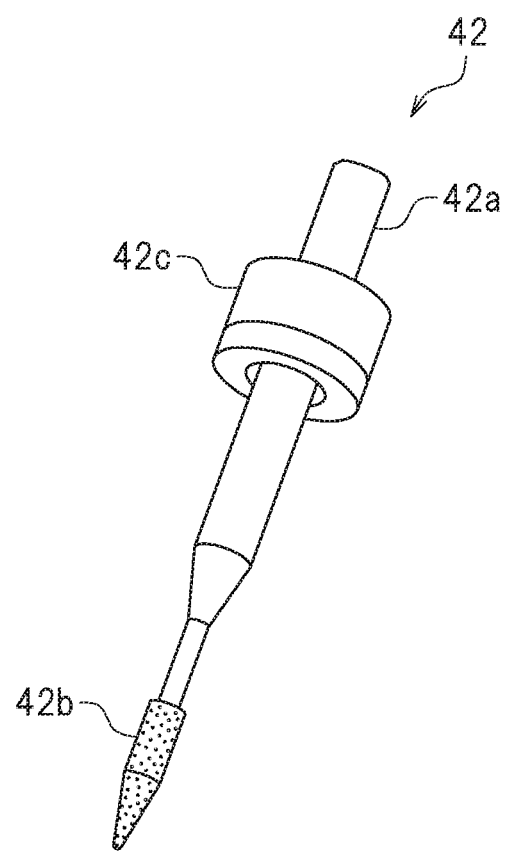
FIG. 8B is a perspective view illustrating a second processing tool according to a preferred embodiment of the present invention.

As illustrated respectively in FIGS. 8A and 8B, the first processing tool 41 and the second processing tool 42 have respective flanges 41c and 42c provided thereon. The flanges 41c and 42c protrude in directions perpendicular or substantially perpendicular to the axes of the rod-shaped processing tools 41 and 42 in a collar shape. Respective upper end portions 41a and 42a of the first and second processing tools 41 and 42, which are provided upward relative to the flanges 41c and 42c, protrude from the stockers 48a with the first and second processing tools 41 and 42 accommodated in the stockers 48 of the magazine 48. A cutter portion 41b is provided downward relative to the flange 41c of the first processing tool 41. A polisher portion 42b is provided downward relative to the flange 42c of the second processing tool 42. The cutter portion 41b and the polisher portion 42b are slenderer than the flanges 41c and 42c. The cutter portion 41b and the polisher portion 42b are able to be accommodated in the stockers 48a. The cutter portion 41b is provided with relatively coarse abrasive grains. The polisher portion 42b is provided with relatively fine abrasive particles. The polisher portion 42b is structured such that, for example, abrasive particles made of silicon carbide are bonded to the lower end of the second processing tool 42 by a silicone rubber as a binder. The lower end of the polisher portion 42b is narrower than the lower end of the cutter portion 41b and pointed in a conical shape.

These processing tools 41 and 42 are driven by a driver including a spindle 44 and a mover 46. The mover 46 is capable of moving the spindle 44 along the Y axis and the Z axis as desired. As mentioned earlier, the magazine 48 as well as the retainer 30 are movable along the X axis by a driver that is not shown in the drawings. This allows the spindle 44 to change its relative position to the magazine 48 and the retainer 30 as desired.

The spindle 44 holds each of the upper end portions 41a and 42a of the first and second processing tools 41 and 42. The spindle 44 moves to a position above the first processing tool 41 accommodated in one of the stockers 48a of the magazine 48 and then descends, so that it can hold the upper end portion 41a of the first processing tool 41. The spindle 44 is able to rotate the first processing tool 41 while holding the first processing tool 41. This enables the first processing tool 41 to rotate about the Z axis. Likewise, the spindle 44 enables the second processing tool 42 to rotate about the Z axis. The first processing tool 41 and the second processing tool 42 are rotated about the Z axis by the spindle 44.

As described previously, the storage or memory 20 and the controller 50 are provided in the rear area of the cutting device 1 (see FIG. 1). The storage or memory 20 stores the first data produced by the data generator 70. The controller 50 controls the operations of the retainer 30 and the cutting mechanism 40. As illustrated in FIG. 1, the controller 50 is configured or programmed to include a first control section 52 and a second control section 54. Such a controller 50 and its various components may be implemented by hardware components, or may be implemented functionally by execution of a computer program by a central processing unit (CPU). For example, the controller 50 and its various components can be implemented by such components as a CPU, a read-only memory (ROM) that stores programs or the like to be executed by the CPU, and a random access memory (RAM), which may be provided, for example, in a known personal computer and a general purpose computer. The ROM stores a program executable to prepare the crown prosthesis C1. The program may be read from, for example, various types of storage media. The storage medium may be, for example, a non-transitory computer readable storage medium, such as compact disk (CD), digital versatile disk, and USB memory, that stores a program to cause a computer to function as the various components described above. The CPU may function as the first control section 52 and the second control section 54, for example, by executing the program stored in the storage medium. A preferred embodiment of the present invention includes a computer program that cuts and polishing processes that causes a computer to function as the above-described components. A preferred embodiment of the present invention also includes a non-transitory computer readable storage medium storing such a computer program. Note that the program may be downloaded via the Internet. The storage or memory 20 may include, for example, a hard disk, a memory, or a circuit. The controller 50 may cause the display 70a to display various information concerning the cutting device 1 and the workpiece.

In the cutting step, the first control section 52 controls the operations of the cutting mechanism 40 and the retainer 30 based on the first data stored in the storage or memory 20 to cut the first member C3 out of the workpiece 5 (i.e., block material 5c). Specifically, the first control section 52 causes the spindle 44 to hold the first processing tool 41 accommodated in one of the stockers 48a of the magazine 48 and to rotate the first processing tool 41. The first control section 52 causes the mover 46 to move the spindle 44. In addition, the first control section 52 causes the retainer 30 to retain the workpiece 5 at a predetermined position and a predetermined angle. The first control section 52 comprehensively controls the timing at which the driver and the retainer 30 operate and the details of the operations thereof as a whole, based on the first data as well as predetermined programs and process conditions. Thus, the cutter portion 41b of the first processing tool 41 that is rotating is brought into contact with the workpiece 5 that is securely retained by the retainer 30. Also, the cutter portion 41b of the first processing tool 41 that is rotating is moved while being kept in contact with the workpiece 5, according to the contour of slice data of the first data.

Therein, the spindle 44 is able to move along the Y axis and the Z axis as desired. Moreover, the retainer 30 is able to move along the X axis and also is able to cause the retained workpiece 5 to rotate in the directions T1 and in the directions T2 as desired. Thus, the first control section 52 is able to three-dimensionally change the relative positional relationship between the workpiece 5 and the first processing tool 41 based on the first data, so that the first control section 52 is able to perform a high-precision cutting process with 5-axis controlling, that is, controlling movement along the X axis, the Y axis, and the Z axis as well as rotation about the X axis and the Y axis. As a result, it is possible to reflect the information contained in the first data accurately in preparing the first member C3. Specifically, it is possible to integrally cut out the crown portion C2 including a recessed portion E and the support portion S protruding from the crown portion C2. For example, it is possible to prepare the crown portion C2 in the disk-shaped block material 5c while keeping the crown portion C2 fixed to the block material 5c (i.e, workpiece 5) by the support portion S.

When the cutting process based on the first data finishes, the first control section 52 controls operations of the spindle 44 and the mover 46 so that the first processing tool 41 held by the spindle 44 can be put into a predetermined one of the stockers 48a of the magazine 48.

For the first processing tool 41, it is possible to provide a plurality of processing tools including cutter portions 41b that are different in material, shape, and size according to the material and contour of the workpiece 5 to be processed. The cutting device 1 is able to use an appropriate processing tool selected for each of the cutting regions based on the first data, for example, in performing a cutting process. In this case, the first control section 52 is able to control the spindle 44 and the mover 46 so as to replace the first processing tool 41 held by the spindle 44 at appropriate timing so that the spindle 44 is able to use an appropriate first processing tool 41 suitable for the cutting region to perform cutting.

S3. Polishing Step

In the polishing step, the second controller 54 controls the operations of the cutting mechanism 40 and the retainer 30 based on the first data stored in the storage or memory 20 to polish the first member C3 that has been cut. Microscopically, the surface of the first member C3 that has been cut may be left with cutting marks, for example, formed along the travel paths of the first processing tool 41. The surface of the crown portion C2 of the first member C3 is desired to have a smooth surface contour that is a specular surface or is close to a specular surface. To achieve this, specifically, the second control section 54 causes the spindle 44 to hold the second processing tool 42 accommodated in one of the stockers 48a of the magazine 48 and to rotate the second processing tool 42. The second control section 54 causes the mover 46 to move the spindle 44. For example, the polisher portion 42b of the second processing tool 42 that is rotating is moved while being kept in contact with the first member C3, according to the contour of STL data of the first data. In this case, it is preferable that the second processing tool 42 be moved along the areas between the travel paths of the first processing tool 41 in the cutting step. In addition, the second control section 54 causes the retainer 30 to retain the first member C3 at a predetermined position and a predetermined angle. The second control section 54 comprehensively controls the timing at which the mover 46 and the retainer 30 operate and the details of the operations thereof as a whole, based on the first data as well as predetermined programs and process conditions. As a result, the polisher portion 42b of the second processing tool 42 that is rotating is able to be brought into contact with the surface of the first member C3. For example, the polisher portion 42b is brought into contact with the apex portions of very small surface irregularities that have inevitably been formed on the surface of the first member C3. For example, a portion of the polisher portion 42b that is relatively flat is brought into contact with the apex portions of the surface irregularities. This enables the surface of the crown portion C2 to be polished to a surface contour that is a specular surface or is close to a specular surface. As a result, it is possible to smooth the very small cutting marks that are inevitably formed by the cutter portion 41b and perform more faithful processing according to the shape designed by CAD (i.e., the final contour).

When the polishing process is completed, the second control section 54 controls operations of the spindle 44 and the mover 46 so that the second processing tool 42 held by the spindle 44 can be put into a predetermined one of the stockers 48a of the magazine 48.

For the second processing tool 42, it is possible to provide a plurality of processing tools that are different in material, shape, and size of the abrasive particles on the polisher portion 42b, according to, for example, the material of the first member C3 which is the workpiece 5, the contour of the crown portion C2, and the level of polishing required. The cutting device 1 can use an appropriate second processing tool selected for each of the polishing surfaces, which is the target of polishing, based on the first data, for example, to polish the surface of the crown portion C2. In this case, the second control section 54 is able to control the spindle 44 and the mover 46 so as to replace the second processing tool 42 held by the spindle at appropriate timing so that the spindle 44 can use an appropriate second processing tool 42 suitable for the polishing surface to perform polishing. For example, the second control section 54 may cause the surface of the crown portion C2 to be polished two or more times with the use of two or more second processing tools 42 having different particle sizes of the abrasive particles provided on the polisher portions 42b.

The first member C3 after being polished is fixed to the workpiece 5 via the support portion S. The crown portion C2 is joined to the support portion S. This means that the operator may cut off the support portion S at the first end portion e1 so that the crown portion C2 is disconnected from the support portion S, to obtain the crown prosthesis C1. The disconnection of the support portion S is not limited to the just-described way, but may be carried out, for example, by a small-sized, portable rotary cutting device called a micromotor (dental electric engine). Thus, the desired crown portion C2 is able to be obtained. It should be noted that when very small disconnection marks due to the disconnection of the support portion S are observed on the tongue side surface of the crown portion C2, the operator may manually polish such disconnection marks. The crown prosthesis C1 from which the support portion S has been removed may be completely sintered at a predetermined sintering temperature. The crown prosthesis C1 contracts to the size of the final contour by the sintering. Thus, the desired crown prosthesis is able to be obtained.

As thus far described, the present preferred embodiment makes it possible not only to cut the crown portion C2 based on three-dimensional data using CAD/CAM technology but also to successively polish, using such three-dimensional data, the surface of the crown portion C2 that has been cut. Thus, the surface of the crown prosthesis C1 before sintering is able to be processed into a smooth surface free of cutting marks. This eliminates the polishing step after sintering of the crown prosthesis C1. As a result, it is possible to reduce the amount of time and effort required for the operator to prepare the crown prosthesis C1. Moreover, it is possible to prepare the crown prosthesis C1 accurately based on three-dimensional data. Furthermore, when the ceramic material such as zirconia is polished before sintering, the crown prosthesis C1 after sintering is allowed to have pleasing and elegant glossy shine. Thus, it is possible to provide the crown prosthesis C1 with higher esthetics.

In the present preferred embodiment, only one support portion S preferably is provided on the tongue side surface of the crown portion C2, and cutting and polishing are carried out while supporting the crown portion C2 by the support portion S. In addition, the support portion S preferably has a cylindrical shape, and each of the first end portion e1 and the second end portion e2 is controlled to have an appropriate cross-sectional diameter. This enables use of the cutting device 1 throughout the process from cutting to polishing without spoiling the esthetics of the crown prosthesis C1. Moreover, the cutting device 1 is able to precisely polish the surface of the crown portion C2, especially the lip side surface thereof. Moreover, the cutting device 1 reduces the disconnection marks of the support portion S on the tongue side surface of the crown portion C2 to a smaller area. As a result, the crown prosthesis C1 with higher esthetics is able to be prepared easily with higher dimensional accuracy.

The present preferred embodiment uses as the workpiece a zirconia-based optically-gradational disk that exhibits high strength and high translucency after sintering and in which the brightness and hue gradually change along its thickness direction, for example. The use of this optically-gradational disk eliminates the need for facing of a porcelain material and enables preparation of the crown prosthesis C1 with even higher esthetics by a full-contour technique. Specifically, in addition to eliminating the trouble of polishing, the number of steps from the cutting is reduced so that a crown prosthesis C1 with an appearance close to a natural tooth can be formed within a short time. Furthermore, the present preferred embodiment enables the cutting process and the polishing process to be precisely carried out based on three-dimensional data. As a result, the thickness of the crown portion C2 itself may be reduced. This allows the abutment tooth C0 to be designed to have a larger size, and consequently reduces the amount of the patient's natural tooth that needs to be removed for forming the abutment tooth C0.

In the foregoing preferred embodiment, the cutting mechanism 40 preferably includes the first cutting tool 41 and the second cutting tool 42 that cuts and polishing the workpiece 5, and the driver that changes the relative position of the first cutting tool 41 and the second cutting tool 42 relative to the workpiece 5. The mover 46 causes the first processing tool 41 and the second processing tool 42 to move along a first axis and a second axis that extend along at least two different directions. In addition, the retainer 30 is capable of moving the workpiece 5 to move along a third axis extending in a direction different from the first axis and the second axis, and is rotatable about at least two different axes. This enables the retainer 30 to move the workpiece 5 relative to the cutting tool 42 freely along the five axes, thus achieving a cutting process with a high degree of freedom. Furthermore, it is possible to prepare a crown prosthesis C1 with superior design precisely.

The foregoing preferred embodiment preferably uses the workpiece 5 made of a zirconia-based ceramic, for example, which is most suitable for preparing an actual crown prosthesis C1 with a full-contour technique. However, the technology disclosed herein is not limited to the technology that uses the workpiece 5 made of zirconia-based ceramic. For example, the workpiece 5 may be made of various materials including: inorganic materials such as alumina-based ceramic, silica-based ceramic, and gypsum; synthetic wax materials such as paraffin wax and polyethylene wax; synthetic resin materials such as polymethyl methacrylate (PMMA); and composite materials such as fiber-reinforced resin materials.

In the foregoing preferred embodiment, the storage or memory 20 and the controller 50 are preferably provided in a rear area of the cutting device 1. However, it is also possible that at least one of the storage or memory 20 and the controller 50 may be provided, for example, external to the case main body 12 of the cutting device 1. For example, at least one of the storage or memory 20 and the controller 50 may be provided inside a personal computer that is used as the data generator 70. Alternatively, it is possible that a ROM (read-only memory) provided in the personal computer used as the data generator 70 may store a program that functionally implements the controller 50 of the data generator 70, and the controller 50 may be implemented by execution of the program by a CPU in the data generator 70 or the cutting device 1.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:
1. A crown prosthesis preparing system comprising:
a data generator producing three-dimensional data representative of a crown prosthesis; and a cutting device including a retainer retaining a workpiece, a cutting mechanism cutting the workpiece, and a controller controlling the retainer and the cutting mechanism; wherein the cutting mechanism includes:
 a first processing tool that cuts the workpiece to form a processed workpiece;
 a second processing tool that polishes the processed workpiece having been cut; and
 a driver detachably holding at least one of the first processing tool and the second processing tool and controlling a position of the at least one of the first processing tool and the second processing tool relative to the workpiece;

the controller is configured or programmed to include:
 a first control section controlling the retainer and the cutting mechanism based on the three-dimensional data to cause the first processing tool to cut the workpiece retained by the retainer, to form the processed workpiece; and
 a second control section controlling the retainer and the cutting mechanism based on the three-dimensional data to cause the second processing tool to polish cutting marks formed by the first processing tool on a surface of the processed workpiece retained by the retainer and to smooth the surface; wherein the second control section causes the second processing tool to polish the cutting marks subsequent to the first control section causing the first processing tool to cut the workpiece.

2. The crown prosthesis preparing system according to claim 1, wherein:
 the data generator produces first data as the three-dimensional data, the first data being three-dimensional data representative of a first member including a crown portion corresponding to the crown prosthesis and a support portion supporting the crown portion;
 the first control section causes the workpiece to be cut based on the first data to form the first member;
 the crown portion is supported on the workpiece with the support portion; and
 the second control section causes a surface of the crown portion to be polished based on the first data.

3. The crown prosthesis preparing system according to claim 1, wherein the workpiece is a semi-sintered compact of zirconia-based ceramic.

4. The crown prosthesis preparing system according to claim 1, wherein the workpiece is an optically-gradational disk including a plurality of stacked layers in which at least one of brightness and hue successively changes.

5. The crown prosthesis preparing system according to claim 2, wherein the data generator produces the first data in which only one support portion is provided on a tongue side surface of the crown portion.

6. The crown prosthesis preparing system according to claim 2, wherein:
 the data generator produces the first data in which the support portion includes:
 a cylindrical shape;
 a first end, being connected to the crown portion and having a cross-sectional diameter of about 2 mm to less than about 3 mm; and
 a second end, being an end opposite to the first end and having a cross-sectional diameter of about 3 mm to about 4 mm.

7. The crown prosthesis preparing system according to claim 1, wherein:

the driver causes the first processing tool and the second processing tool to move along at least a first axis and a second axis, the first axis and the second axis extending in different directions from each other; and the retainer causes the workpiece to move along a third axis extending in a direction different from the first axis and the second axis and to rotate about at least two different axes.

8. A method of preparing a crown prosthesis using a crown prosthesis preparing system including a data generator producing three-dimensional data representative of the crown prosthesis; and a cutting device including a retainer retaining a workpiece, a cutting mechanism, and a controller controlling driving of the retainer and the cutting mechanism, the cutting mechanism including a first processing tool that cuts the workpiece to form a processed workpiece, a second processing tool that polishes the processed workpiece having been cut, a driver detachably retaining at least one of the first processing tool and the second processing tool and controlling a position of the at least one of the first processing tool and the second processing tool, the method comprising:

producing three-dimensional data representative of the crown prosthesis;

causing the first processing tool to cut the workpiece retained by the retainer to form the processed workpiece by controlling the retainer and the cutting mechanism based on the three-dimensional data; and causing the second processing tool to polish cutting marks formed by the first processing tool on a surface of the workpiece retained by the retainer and to smooth the surface by controlling the retainer and the cutting mechanism based on the three-dimensional data; wherein the second processing tool polishes the cutting marks subsequent to the first processing tool cutting the workpiece.

9. A non-transitory computer-readable storage medium storing a program executable in a crown prosthesis preparing system including a data generator producing three-dimensional data representative of a crown prosthesis; and a cutting device including a retainer retaining a workpiece, a cutting mechanism, and a controller controlling driving of the retainer and the cutting mechanism, the cutting mechanism including a first processing tool that cuts the workpiece to form a processed workpiece, a second processing tool that polishes the processed workpiece having been cut, a driver detachably retaining at least one of the first processing tool and the second processing tool and controlling a position of the at least one of the first processing tool and the second processing tool, the program causing the crown prosthesis preparing system to perform a method comprising:

storing three-dimensional data representative of the crown prosthesis;

causing the first processing tool to cut the workpiece retained by the retainer so as to form the processed workpiece by controlling the retainer and the cutting mechanism based on the three-dimensional data; and causing the second processing tool to polish cutting marks formed by the first processing tool on a surface of the workpiece retained by the retainer and to smooth the surface by controlling the retainer and the cutting mechanism based on the three-dimensional data; wherein the second processing tool polishes the cutting marks subsequent to the first processing tool cutting the workpiece.

* * * * *

UNITED STATES PATENT AND TRADEMARK OFFICE
CERTIFICATE OF CORRECTION

PATENT NO. : 10,172,694 B2
APPLICATION NO. : 15/704127
DATED : January 8, 2019
INVENTOR(S) : Sachino Isobe et al.

It is certified that error appears in the above-identified patent and that said Letters Patent is hereby corrected as shown below:

In the Claims

Claim 9, Column 16, Line 9 (Line 59) should be corrected as follows:
"…retained by the retainer to form the processed…"

Signed and Sealed this
Ninth Day of April, 2019

Andrei Iancu
*Director of the United States Patent and Trademark Office*